(12) United States Patent  (10) Patent No.: US 7,842,263 B2
Hill  (45) Date of Patent: Nov. 30, 2010

(54) SANITIZING AND DAMPENING CONTAINER (76) Inventor: Karlene Hill, 12316 New Hampshire Ave., Silver Spring, MD (US) 20904

( * ) Notice: Subject to any disclaimer, the term of this patent is extended or adjusted under 35 U.S.C. 154(b) by 84 days.

(21) Appl. No.: 12/359,500

(22) Filed: Jan. 26, 2009

(65) Prior Publication Data

US 2009/0238718 A1  Sep. 24, 2009

Related U.S. Application Data (63) Continuation-in-part of application No. 12/076,669, filed on Mar. 21, 2008.

(51) Int. Cl.
*A61L 2/00* (2006.01)
(52) U.S. Cl. ...................................... 422/300
(58) Field of Classification Search .................. 422/28, 422/300, 301; 206/207; 15/261
See application file for complete search history.

(56) References Cited

U.S. PATENT DOCUMENTS 1,016,119 A  1/1912  Whitmore
4,831,681 A  5/1989  Puder
4,948,078 A  8/1990  Dumenigo
5,148,951 A  9/1992  Moure et al.
7,041,261 B2  5/2006  Margolis
2005/0071942 A1 *  4/2005  Akhtar .................... 15/257.01

* cited by examiner

*Primary Examiner*—Walter D Griffin
*Assistant Examiner*—Timothy Cleveland
(74) *Attorney, Agent, or Firm*—The Law Firm of Andrea Hence Evans, LLC (57) ABSTRACT An apparatus for sanitizing or dampening objects comprising a container having corner pockets that support springs is provided. Springs are extended upwardly from the corner pockets. A platform is positioned above container, wherein pocket covers on the platform are aligned with the springs and substantially cover them. The platform is adapted to support the object to be sanitized or dampened. When a pressure is applied to the platform, the platform can move downward into a solution contained in the container, dampening or sanitizing the object supported by the platform. A cover is sized to cover an opening on the platform. Alternatively, the cover can be housed underneath the container.

11 Claims, 7 Drawing Sheets

SANITIZING AND DAMPENING CONTAINER

RELATED APPLICATIONS

The present application is a continuation-in-part of prior U.S. application Ser. No. 12/076,669, filed Mar. 21, 2008, the entirety of which is incorporated herein by reference.

FIELD OF THE INVENTION

This invention relates to a container for dampening and sanitizing objects often contaminated in the kitchen, such as a sponge. The container can support the object while not in use, and when necessary, dampen the object with a sanitizing fluid substance.

BACKGROUND OF THE INVENTION

Objects used to clean surfaces and dishware in the home, such as sponges or dish rags, are often the source of bacteria in the kitchen and around the house. These sponges or dish rags are not properly cleaned or sanitized often by the users. They can cause contamination on the surfaces in contact with them and even the users hands handling the sponges or dish rags. Sponges or dish rags are typically left on the sink or counter to dry. However, this drying method tends to leave waste on the sponges or dish rags that cause harmful bacteria and mold to form.

Although conventional methods of handling a sponge are effective, they do not address or solve the difficulties associated with drying and sanitizing sponges. Various sponge sanitizers are currently in use, but they do not provide a container that can house sponges of various sizes while not in use and allow them to dry on a sterile surface. Also, these methods do not provide a container with a suspended platform that moistens and sanitize the sponges with a sanitizing fluid to aid in prevention the formation of harmful bacteria and mold.

SUMMARY OF THE INVENTION

It is the object of the present invention to provide an inexpensive yet decorative apparatus to sanitize or moisten contaminated household cleaning objects of various shapes and sizes such as a sponge or dish rag.

It is a further object of the present invention to provide an apparatus where the user can control the amount of fluid substance added to the object such as a sponge or dish rag based on the amount of pressure exerted on the platform.

It is another object of the present invention to provide an apparatus with a platform adapted to support the object to be moistened or sanitized when in use and also support the object when drying on the platform.

The present invention discloses an apparatus for sanitizing or dampening an object such as a sponge, for example. A sponge is used as an example of an object to be dampened or sanitized. Any object desired by the user can be supported on the platform. In particular, the apparatus comprises a container with pocket covers that house springs. A platform supports the object. It will be clear from the description below that many other shapes of the apparatus could also be adopted based on the size and design of the object to be cleaned. For example, the container and platform may be circular, square, rectangular, to name a few. The apparatus preferably uses two to four springs, however, additional springs could be added to further support the platform and to provided added suspension. The apparatus is preferably manufactured out of a stainless steel, metal, ceramic, glass or plastic material. However, the apparatus material can be made from the same materials and have the same design prints as other household items such as soap dishes or appliances so that the apparatus can coordinate with other items in its surrounding area. Lastly, the fluid substance contained in the container can be a disinfecting or cleaning solution known in the art such as a combination of soap and water or a bleach or ammonia based solution.

In one preferred embodiment, a container comprising at least four corner pockets is described. Springs extend upwardly from the corner pockets. A platform having apertures is positioned over the container such that pocket covers cover the springs. The container also has a lid used to aid in preventing dust and debris from entering the container. The lid is sized to act as a cover for the top portion of the platform and sized to act as a support for the bottom of the container. Cover apertures are located on the cover and provide additional air to flow in and out of the apparatus.

BRIEF DESCRIPTION OF THE DRAWINGS

The operation, features and advantages of the present invention should be apparent and fully understood when the following description is read in light of the accompanying drawings in which.

DETAILED DESCRIPTION OF THE INVENTION

Figure 1:
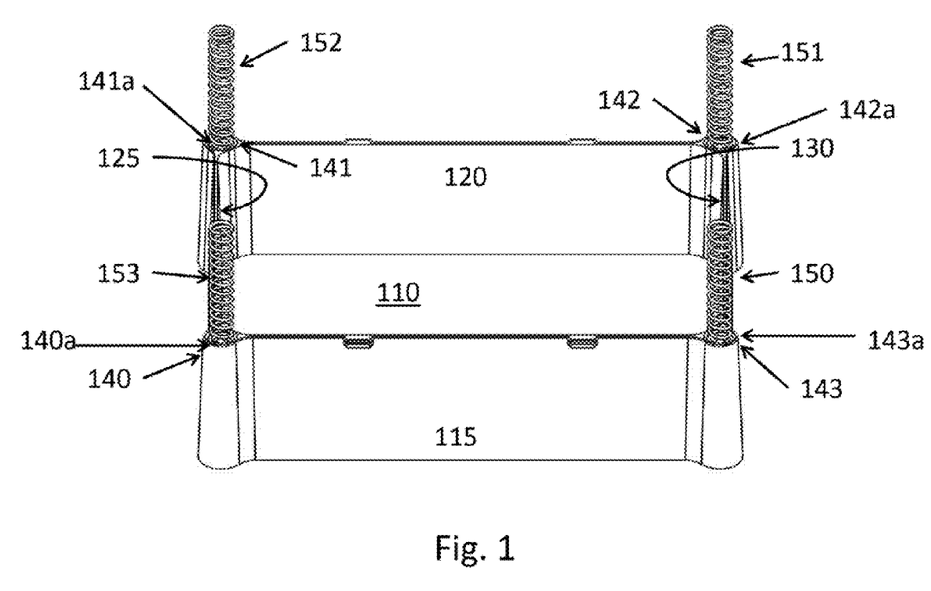
FIG. 1 is a perspective view of the container.

FIG. 1 is a perspective view of the container 100. The container 100 has a bottom 110, a front wall 115, a back wall 120, and a first side wall 125 and second side wall 130. The first 125 and second walls 130 extend upwardly from the bottom 110 to form a rectangular container. Although the container shown in FIG. 1 is rectangular in shape, obvious shape variations can be made as desired. The container 100 houses or supports a fluidic substance. The substance is a solution that will dampen or sanitize the object to be moistened. Any known cleaning solution in the art may be used. Markers may be provided along the inside of the walls of the container to provide the user with a fill line. This will aid in an adequate amount of the substance being placed in the container.

The container 100 further comprises corner pockets 140, 141, 142 and 143. These pockets 140, 141, 142 and 143 are located at each corner of the container 100. The corners of the containers are where the side walls 125 and 130 meet with the front 115 and back wall 120. For description purposes corner pocket 140 will be discussed. Corner pockets 141, 142 and 143 are identical in shape, size and function as corner pocket 140. Corner pocket 140 extends towards the outside of the container 100. The inside of the container 100 is considered the area where the substance is provided. The corner pocket 140 is cylindrical in shape. The corner pocket 140 is the same height as the container 100 such that the opening 140a is flush with the side wall 125 and front wall 115. Similarly, corner pockets 141, 142 and 143 comprise openings 141a, 142a, 143a, respectively. The corner pockets 140, 141, 142 and 143 support a base or bottom of springs 153, 152, 151 and 150 respectively. The base is the portion of the spring that is inserted into the corner pockets. At least 0.25 inches of the spring is supported in the corner pocket. The diameter of the springs 153, 152, 151 and 150 is smaller than the diameter of the corner pocket openings 140a-143a so that the springs can fit into the openings. Or the diameter of the openings on the corner pocket are larger than the diameter of the springs so that the springs are supported properly. The shape of the corner pocket may be altered so long as the base of the spring used with the container is identical with the shape of the opening of the pocket so that the springs can be supported.

The springs 153, 152, 151, 150 extend upward from the corner pockets 140-143, respectively. The compression springs have a free length of at least 1.5", an outer diameter of 0.24" and a wire size of 0.02". They exert a linear force of 1.49 lbf/in. Springs of various sizes may be used and the corner pockets will be sized to accommodate them. The springs 153, 152, 151 and 150 extend at least 1.25 inches out of the container 100, as measured from the corner pocket. The springs support the platform 200 shown in FIG. 2 when the platform 200 is positioned above the container 100.

Figure 2:
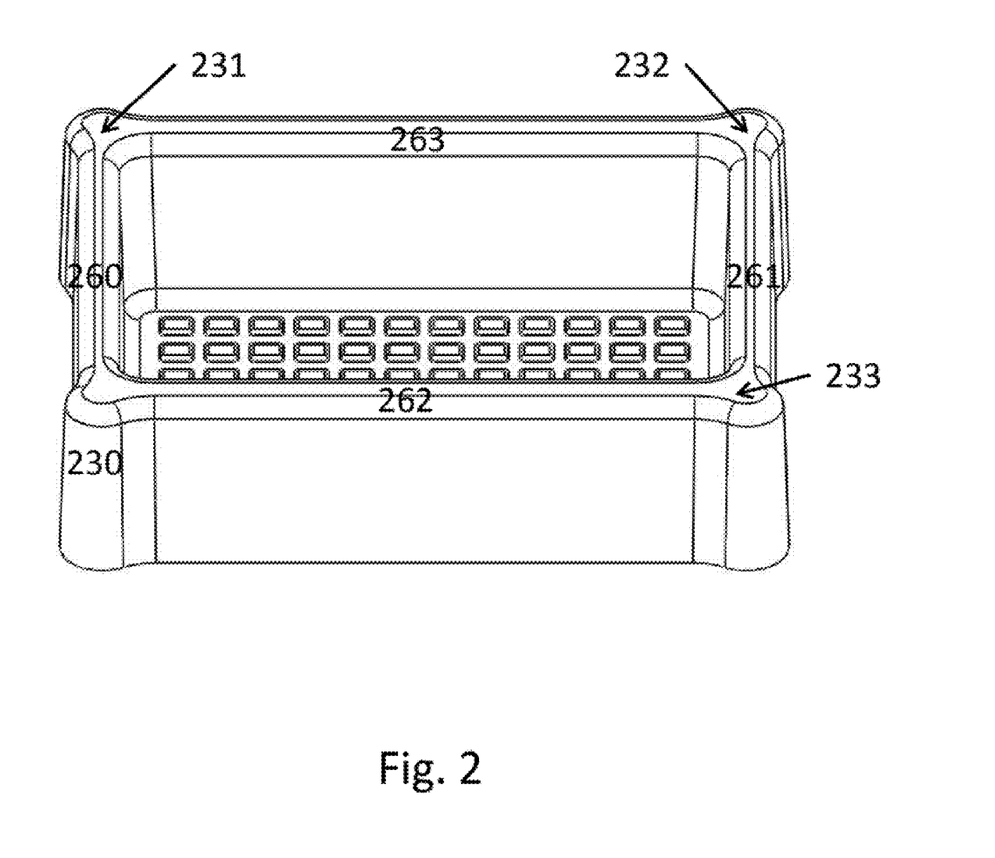
FIG. 2 is a perspective view of the platform.
Figure 3:
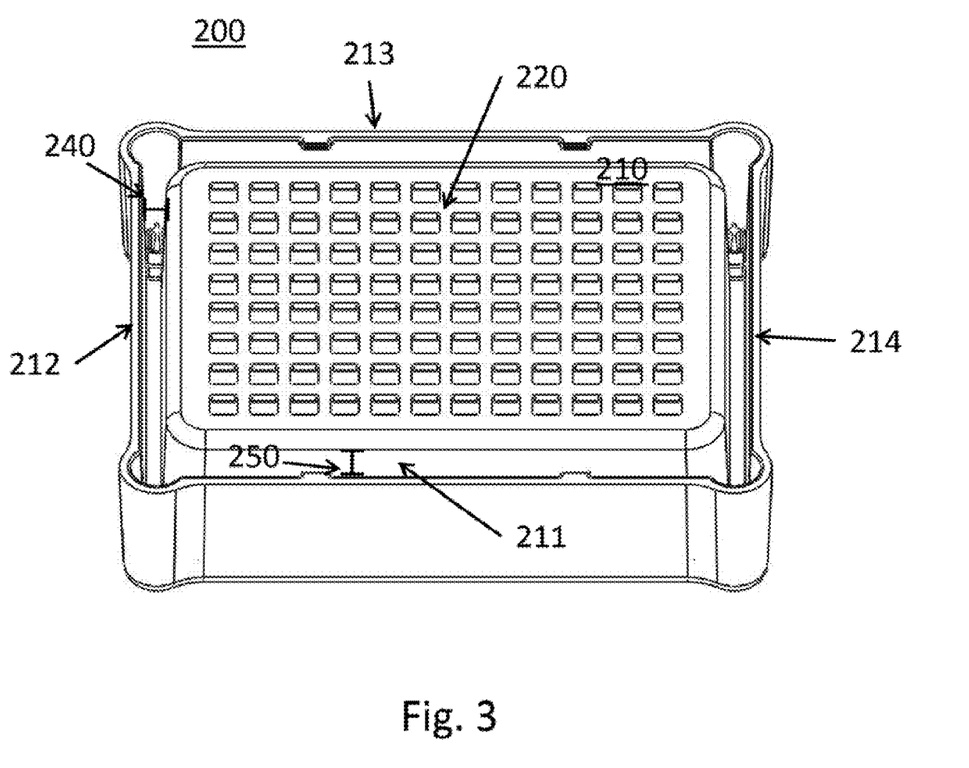
FIG. 3 is a perspective view the bottom of the platform in FIG. 2.

As shown in FIG. 2, the platform 200 comprises a platform base 210 and platform walls 211, 212, 213 and 214 (shown in FIG. 3). The platform base 210 is sized to fit inside the container 100. The platform base 210 is the same shape as the bottom 110 of the container 100. The platform base 210 is smaller than the bottom 110 of the container to ensure the platform base 210 will fit inside the container 100 and be supported by the bottom 110. The platform base 210 further comprises apertures 220. The apertures 220 allow the substance in the container 100 to enter the platform and moisten the object on the top side of the base 210. A lip 224 extends over all side walls 211-214 of the platform 200. The lip 225 extends downward and is folded over such that only the platform base 210 and walls 211-214 are in contact with the solution in the container. The lip 225 extends over the front 115, back 120 and first 125 and second walls 130 of the container 100 when the platform 200 is connected to the container 100. The lip 225 is molded onto the platform 200 so that they form a one-piece structure.

FIG. 3 is a perspective view the bottom of the platform in FIG. 2. The platform 200 has been flipped over to provide better view of walls 211-214. Furthermore, the side wall extensions 240 are shown. The side wall extension 240 is the area of the lip 225 between the side wall 212 and the side lip ledge 260 or between the side wall 214 and the side lip ledge 261. The side wall extension 240 is equal on both sides. The front and back wall extensions 250 are the areas of the lip 225 between the front platform wall 211 and the front lip ledge 262 or the area of the lip 225 between the back platform wall 213 and the back lip ledge 263. The front and back wall extension 250 are equal to each other.

The lip 225 further comprises pocket covers 230, 231, 232 and 233, wherein the pocket covers fit over the tops of the springs 153, 152,151, and 150 respectively. The portion of the springs 150-153 that are exposed or not covered by the corner pockets 140-143 is covered by the pocket covers. The pocket covers 230-233 are located in the corners of the lip. Where the front lip ledge 262 meets the side lip ledge 260 forms corner pocket 230. Where the front lip ledge 262 meets the side lip ledge 261 forms corner pocket 233. Similarly, where back lip ledge 263 meets side lip ledge 260 forms corner pocket 231 and where back lip ledge 263 meets side lip ledge 261 forms corner pocket 232. The pocket covers 230-233 act as a cap over the springs 150-153. The pocket covers 230-233 substantially cover the springs 150-153 in the corner pockets 140-143. The springs 150-153 being positioned in the pocket covers 230-233 essentially connects the platform 200 to the container 100. The pocket covers 230-233 align with the springs 150-153 when the platform 200 is supported by the container 100. The tops of the walls of the container fit underneath the ledges of the container 100. The tops of the walls of the container 100 fits in the extension areas of the lip 225. When the platform 200 is connected to the container 100, there is minimal horizontal movement of the container 100. The container 100 and platform 200 are fitted so that only vertical movement of the platform 200 is provided. The user may lift the container to move it to another physical location, if desired. However, during use, to avoid spillage of the substance, the container 100 remains stable and secured to the platform 200.

Figure 4:
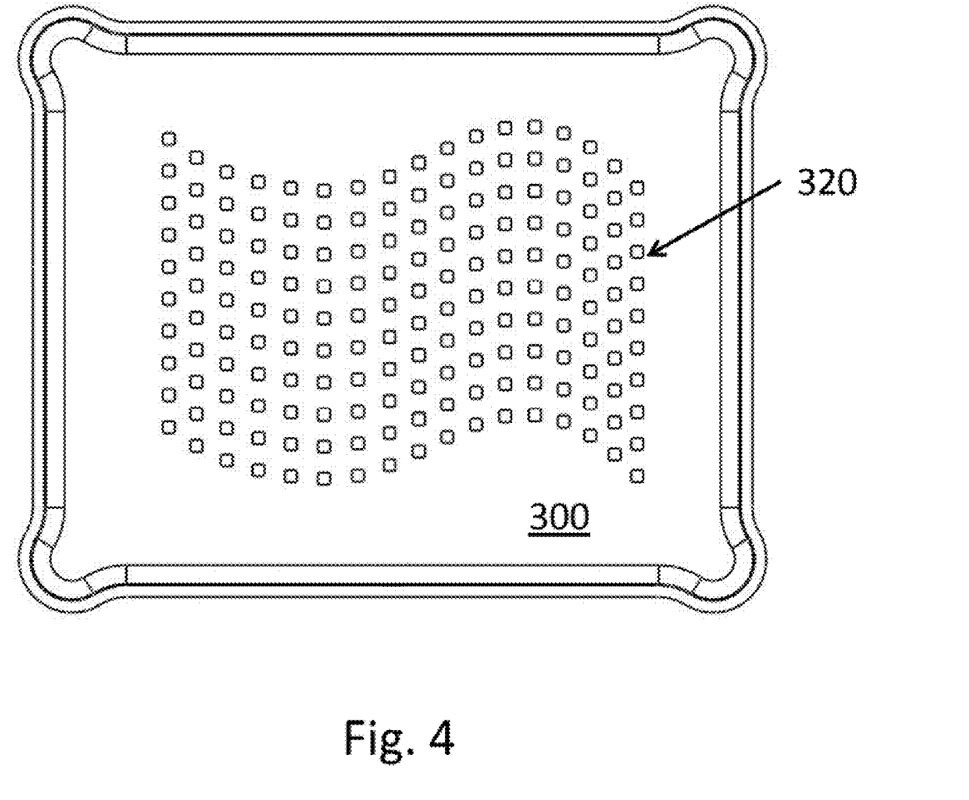
FIG. 4 is a perspective view of the cover.
Figure 5:
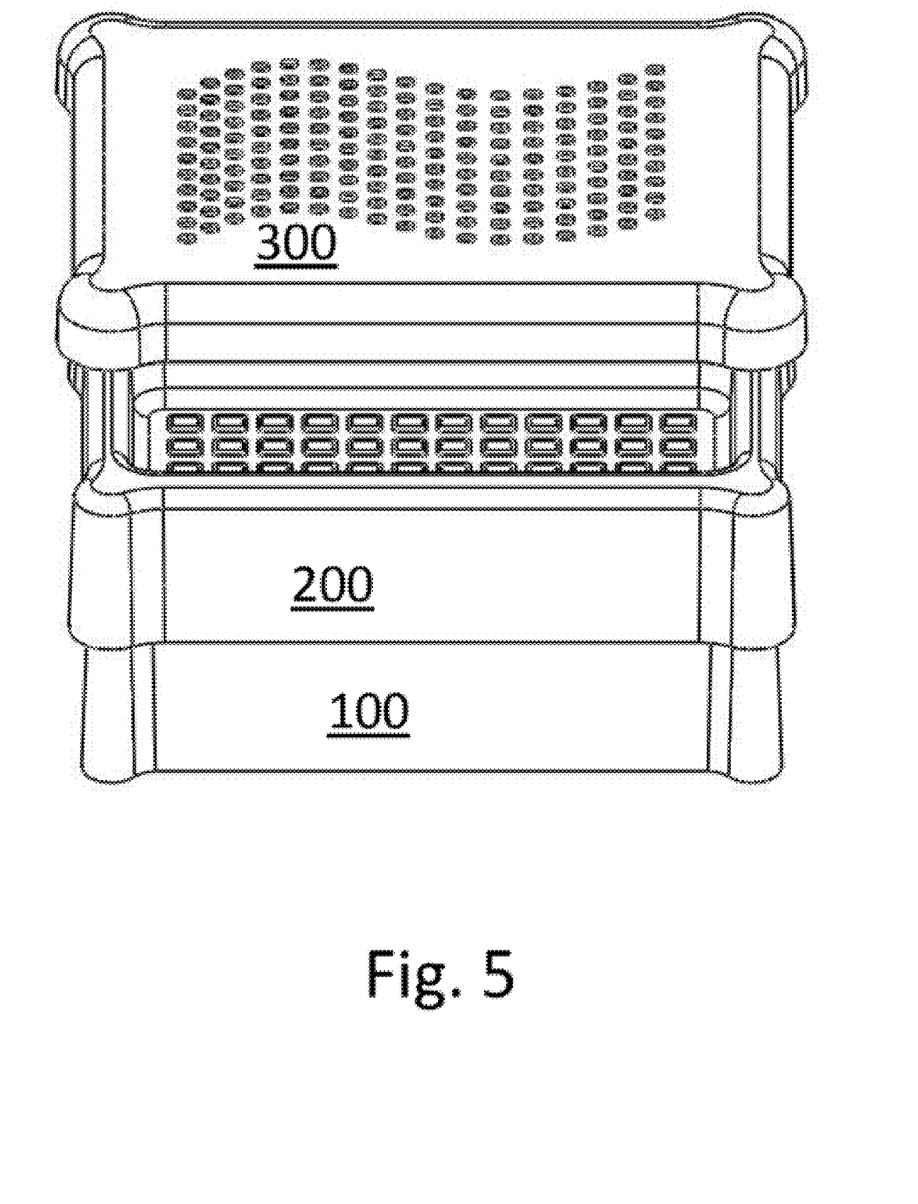
FIG. 5 is a perspective view of the cover, platform and container.

FIG. 4 is a perspective view of the cover 300. The cover 300 is sized to fit over an opening on the platform 200 (as shown in FIG. 5). The cover 300 sides are equal in length to the length of the front, back and side lip ledges 260-263. The cover 300 snaps onto the platform 200 and is secured along the lip 225 of the platform 200. The cover 300 further comprises cover apertures 320. The cover apertures 320 allow air to enter and exit the apparatus to aid in airflow and aid in drying the object to be moistened. Furthermore, the cover apertures 320 aid in preventing bacteria and mold from forming on the object while the object is resting on the platform and while the apparatus is not in use. If the user desires not to use the cover 300 while exerting pressure on the platform 200, the cover 300 is sized to fit underneath the apparatus-such that the cover 300 is flipped and placed underneath the bottom 110 of the container 100.

FIG. 5 is a perspective view of the cover 300, platform 200 and container 100 which together form an apparatus for sanitizing or dampening objects. An object to be moistened or sanitized is placed onto the top of the platform base 210. The platform 200 used separate from the container 100 or connected to the container 100. For example, the platform 200 can be placed into a solution, where the solution can be located in a sink or pan. The solution will enter the platform and moisten the object through the apertures 220 on the platform 220. Preferably, the platform 200 is connected to the container 100, as described above. The object is placed on the top of the platform base 210 inside the platform 200. When no pressure is exerted on the platform 200, the platform appears to float above the area where the liquid is provided in the container 100. That is, solution does not flow through the apertures until the user exerts a downward pressure on the platform 200. The springs 150-153 move downward a distance to allow the base 210 of the platform 200 to enter into the solution. If the user fills the container past the fill line provided, the water is likely to enter the platform base 210 through the apertures 220 without any pressure. However, it is desired that the object can remain on the platform base 210 until ready to be sanitized. The user can exert a downward pressure on the object to be sanitized which will move the platform 210 downward, since the object rest on the platform. Because the pocket covers 230-233 substantially cover the springs 150-153, the user will not have to worry about fingers getting caught in the spring. Also, the object to be sanitized will never enter the springs because of the lip and pocket covers covering the springs. To avoid having to touch the object being sanitized and to avoid making a mess, it is desired that the cover 300 be placed over the platform 200 while connected to the container 100. After the object is placed in the platform 200, the cover 300 can be applied. Then, pressure can be downwardly exerted on the cover so that only the cover 300 and the attached platform 200 move downward by the springs 150-153 allowing the solution to enter the apertures 220 on the platform 220 and the object sitting on the top of the platform to be sanitized.

Figure 6:
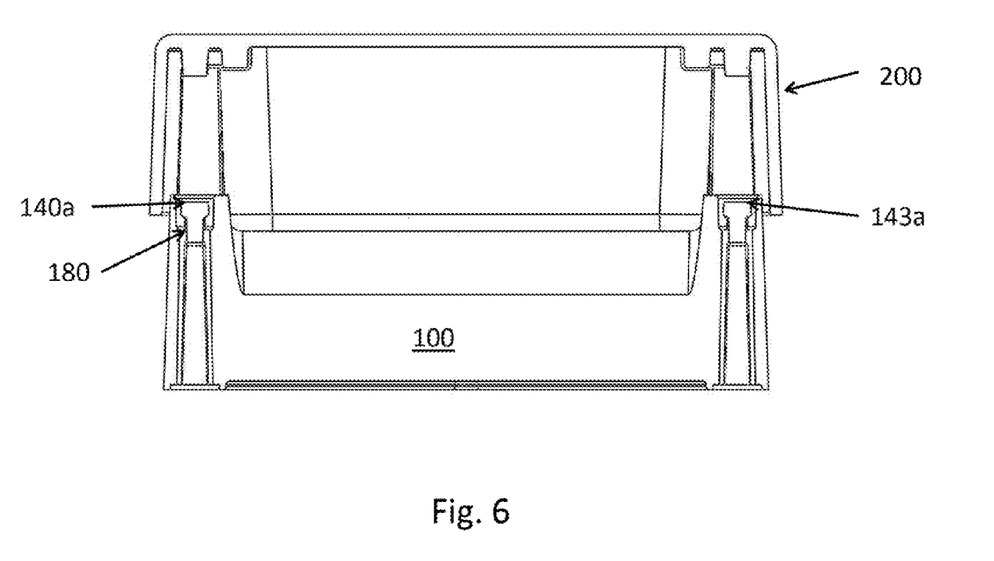
FIG. 6 is a cross section of the platform and container.
Figure 7:
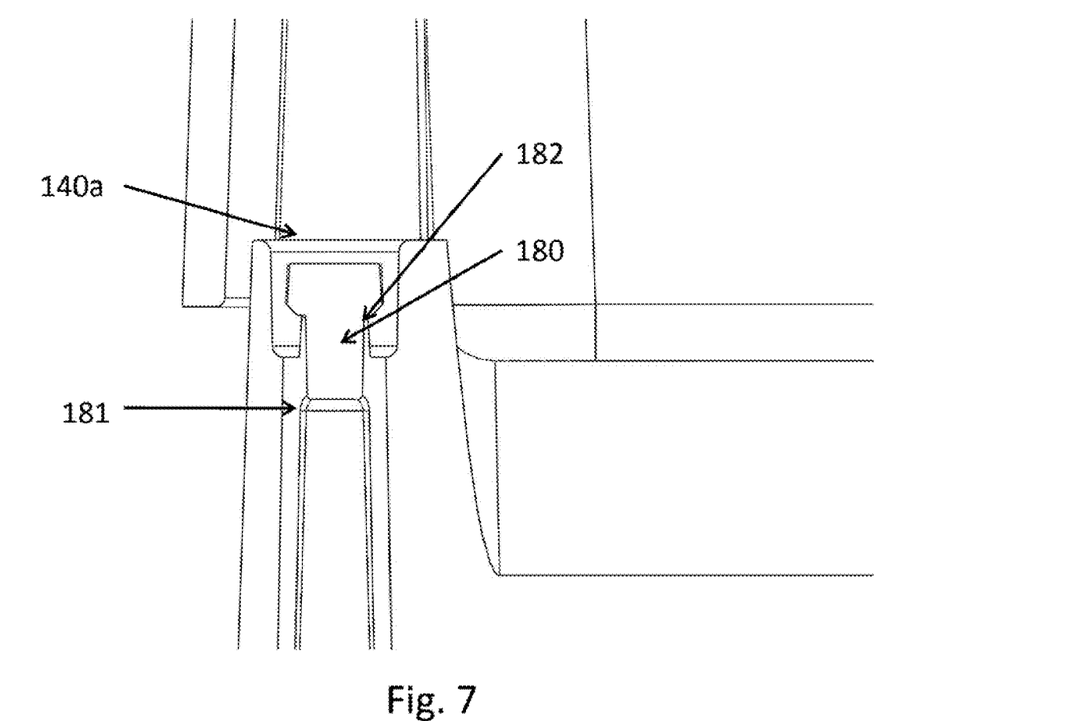
FIG. 7 is a cross section of the spring assembly.

FIG. 6 is a cross section of the platform 200 and container 100. The openings 140a and 143a are shown, along with a spring assembly 180. The springs fit inside their respective opening on the container and when the platform 200 is placed above the springs, the platform's pocket covers fit over the springs. FIG. 7 is a cross section of the spring assembly 180. For illustration purposes, opening 140a is illustrated and discussed. However, all openings 140a-143a are identical is size, shape, function and structure. To ensure the springs stay in place, a small lip 182 is positioned at the bottom of the opening 140a. This lip 182 helps secure the springs and will not allow them to fall out during disassembly. You will, however, be able to remove them if you pull the springs or exert a force on the springs. A spring stopper 181 is provided inside the opening also. Because it is desired that a portion of the spring remain outside the container, it is necessary to have the spring stopper 181. The stopper 181 prevents the spring from moving further inside the opening. The stopper extends is positioned a distance inside the opening and extends downward to the bottom of the container. So that the container does not unnecessarily move, suction cups or another material that provides friction may be placed at the bottom of the container.

It will be understood that the above description of the present invention is susceptible to various modifications, changes and adaptations, and the same are intended to be comprehended within the meaning and range of equivalents of the appended claims.

The invention claimed is:

1. An apparatus for sanitizing or dampening objects comprising:
   a container having a bottom, a front wall, a back wall, and a first and second side wall, wherein the first and second walls extend upwardly from the bottom; and
   at least one corner pocket in each corner of the container, wherein the at least one corner pocket supports a base of at least one spring such that the base of the at least one spring is in the corner pocket and a top of the at least one spring extends outside the container;
   a solution in the container;
   wherein the spring does not come into contact with the solution.

2. The apparatus of claim 1, wherein a diameter of the corner pocket is larger than a diameter of the spring to support the spring.

3. The apparatus of claim 1 further comprising a platform, wherein the platform comprises a platform base, wherein the platform base is sized to fit inside the container.

4. The apparatus of claim 3, wherein the platform base comprises apertures.

5. The apparatus of claim 3, wherein the platform further comprises a lip, wherein the lip extends over all sides of the platform such that the lip extends over all walls of the container when the platform is connected to the container.

6. The apparatus of claim 5, wherein the lip further comprises pocket covers, wherein the pocket covers fit over the top of the at least one spring.

7. The apparatus of claim 1 further comprising a cover sized to fit over an opening on a platform, the cover further comprising cover apertures.

8. An apparatus for supporting an object comprising: a container having at least a first, second, third and fourth corner pocket formed where container side walls meet with a front and back wall of the container; wherein the corner pockets support a first, second, third and fourth spring, respectively, wherein the springs extend upward from the corner pockets; and a platform, wherein the platform comprises a platform base, wherein the platform base is sized to fit inside the container, wherein the platform has a lip that extends over the side walls of the container, wherein the lip further comprises ledges that meet to form pocket covers, wherein the pocket covers receive the springs in the corner pockets when the platform is attached to the container.

9. The apparatus of claim 8 wherein the platform base has the same shape as a bottom of the container.

10. The apparatus of claim 9, wherein a removable object is positioned on a top of the platform base.

11. The apparatus of claim 8 further comprising a cover sized to fit over an opening on the platform or the bottom of the container.

* * * * *